United States Patent [19]

Dawson et al.

[11] Patent Number: 4,546,110

[45] Date of Patent: Oct. 8, 1985

[54] PHEROMONES

[75] Inventors: Glenn W. Dawson, Houghton Regis; David C. Griffiths, Harpenden; John A. Pickett, Kimpton, all of England

[73] Assignee: National Research Development Corporation, England

[21] Appl. No.: 463,875

[22] PCT Filed: May 28, 1982

[86] PCT No.: PCT/GB82/00156

§ 371 Date: Jan. 20, 1983

§ 102(e) Date: Jan. 20, 1983

[87] PCT Pub. No.: WO82/04249

PCT Pub. Date: Dec. 9, 1982

[30] Foreign Application Priority Data

May 28, 1981 [GB] United Kingdom ............... 8116357

[51] Int. Cl.$^4$ ............... C07C 61/35; C07C 69/75; C07C 175/00; A01N 49/00

[52] U.S. Cl. ............... 514/529; 514/574; 514/690; 514/110; 514/247; 514/412; 514/417; 514/446; 514/470; 544/224; 548/472; 548/479; 548/515; 549/240; 549/247; 549/87; 560/76; 560/127; 560/128; 562/509; 562/510; 568/12; 568/377

[58] Field of Search ............... 560/128, 76, 127; 568/377; 562/509, 510; 424/305, 317, 331

[56] References Cited

U.S. PATENT DOCUMENTS

| 3,517,104 | 6/1970 | Minieri | 424/288 |
| 3,766,209 | 10/1973 | Emmick | 549/2 |
| 3,825,661 | 7/1974 | Emmick | 549/43 |
| 3,845,088 | 10/1974 | Findlay | 568/37 |
| 3,930,023 | 12/1975 | Emmick | 424/330 |
| 4,007,137 | 2/1977 | Sanders et al. | 568/44 |

FOREIGN PATENT DOCUMENTS

| 73080 | 3/1983 | European Pat. Off. . |
| 896039 | 5/1962 | United Kingdom . |
| 1009289 | 11/1965 | United Kingdom . |
| 1056821 | 2/1967 | United Kingdom . |

OTHER PUBLICATIONS

Anet, Aust. J. Chem., vol. 23, 1970, pp. 2101-2108.
Brieger, J. Org. Chem., vol. 32, 1967, p. 3720.
Bowers et al., J. Insect. Physiol., vol. 23, 1977, pp 697-701.
Greenway et al., Ent. Exp. & Appl., vol. 24, 1978, pp 169-174.
Griffiths et al., Ent. Exp. & Appl., 27, (1980), 199-201
March, Advanced Organic Chemistry, 2nd ed., (1977) pp. 761-766.
Rothamsted Report for 1980, Part 1, Jun. 1981, p. 126

Primary Examiner—Donald G. Daus
Assistant Examiner—William A. Teoli, Jr.
Attorney, Agent, or Firm—Jacobs & Jacobs

[57] ABSTRACT

Compounds which are $\beta$-farnesene derivatives obtainable as a Diels-Alder adduct of $\beta$-farnesene and a dienophile or by a modification of such an adduct in a manner as defined herein are of value in pest control, particularly in the control of aphids.

53 Claims, No Drawings

PHEROMONES

This invention relates to derivatives of (E)-β-farnesene, to the production of (E)-β-farnesene and of the derivatives, and to their use in insect control.

The sesquiterpene, (E)-β-farnesene (1), is the main component of the alarm pheromone of many species of aphid and it has been suggested that this compound might be used in aphid control.

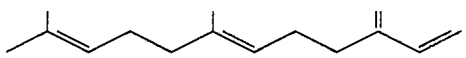

The suggestions have included the use of the alarm pheromone to increase the effectiveness of insecticidal sprays by increasing mobility of aphids and thereby increasing contact with the toxicant, the dispersion of aphids from their feeding sites by treating these sites with the pheromone and the restriction of virus spread by aphids through similar treatment. Whilst experiments have suggested that the use of the pheromone in conjunction with insecticides might have some potential value, the value of its application to feeding sites is severely limited by the tendency of aphids to recolonise the feeding sites fairly rapidly coupled with the volatility of (E)-β-farnesene and its very high sensitivity to aerial oxidation.

The instability of many pheromones has presented a long standing problem to their use in pest control and many methods have been employed for formulating pheromones in order to counter their instabilty. We have used a quite different approach and have found that it is possible to prepare derivatives of (E)-β-farnesene which are active and which are sufficiently stable to be used in approaches to aphid control such as the restriction of virus spread where the instability of (E)-β-farnesene renders the parent compound itself of little value.

Accordingly the present invention comprises a β-farnesene derivative which is obtainable as a Diels-Alder adduct of β-farnesene and a dienophile or by modification of such an adduct in a manner as defined hereinafter.

Whilst the activity of the natural pheromone resides in the (E) or trans compound it is not necessarily the case with the compounds of the present invention that adducts of (Z)-β-farnesene are devoid of worthwhile activity. It will be seen from the Examples that the adducts are for convenience prepared from a mixture of (E)- and (Z)-β-farnesene in which the (E) form is the major component so that the (E) derived compound therefore predominates in the mixture of Diels-Alder adducts obtained. However, although the invention is discussed hereinafter with particular reference to the (E)-β-farnesene adducts it is possible that the (Z) derived compounds may contribute some activity to the mixture.

In the Diels-Alder reaction, the terminal 1,3-diene system of the (E)-β-farnesene reacts with the dienophile forming an (E)-β-farnesene derivative of formula (2)

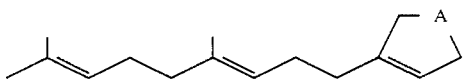

wherein A represents the residue of the dienophile. A wide variety of electron deficient dienophiles may be used in forming (E)-β-farnesene derivatives according to the present invention. The most common forms of dienophile contain a carbon-carbon double or triple bond, a nitrogen-nitrogen double bond or a nitrogen-oxygen double bond with at least one electron withdrawing group attached to at least one of the multiply bonded carbon or nitrogen atoms. In practice dienophiles are often used in which each multiply bonded atom carries such a group. Examples of such electron withdrawing groups include various groups comprising a carbonyl group linked to another organic group, such as groups CO.OR in which R is a monovalent aliphatic hydrocarbon group which may, for example, contain a group R such as methyl, ethyl, decyl, octadecyl or other groups of this type described hereinafter; aryloxycarbonyl groups, for example phenoxycarbonyl; groups C.OR in which R is as just defined and which may, for example, contain alkyl groups as just described; aryl carbonyl groups, for example phenylcarbonyl; carboxyl; formyl; and carbonyloxycarbonyl, carbonyliminocarbonyl or other divalent groups which are joined to both of the multiply bonded atoms. Specific examples of such dienophiles which are of some particular interest are diethyl maleate, didecylmaleate, diethyl acetylene dicarboxylate, didecyl acetylene dicarboxylate, diethyl azodicarboxylate and other related diesters containing two ester groups CO.OR or one ester group CO.OR and a second CO.OR' as discussed hereinafter: azodicarboxylic acid, particularly maleic acid and especially acetylene dicarboxylic acid diesters containing ester groups derived from dihydroxy alcohols of the type HO—$(CH_2CH_2O)_{n'}$H in which n' is preferably an integer as discussed hereinafter; 1,2-bis-(tridecanoyl)-ethylene, 1,2-bis-(tridecanoyl)-acetylene and related diketones; acetylene dicarboxylic acid, maleic acid and particularly maleic anhydride; maleimide and derivatives thereof in which the nitrogen atom is substituted by a group CO.OR in which R may be as referred to above and particularly the compound N-methoxycarbonylmaleimide; methylethenyl ketone and acrolein (propenol). Other examples of suitable dienophiles include alk-2-yn-1-oic acids, R.C≡C—$CO_2$H, which may contain groups R as referred to above, and discussed in more detail hereinafter, particularly saturated groups of 1 to 18 carbon atoms or even more, for example the compound hex-2-yn-1-oic acid; cinnamic acid esters and acrylic acid esters which may both contain groups CO.OR as referred to above and discussed in more detail hereinafter; mesityl N-oxide; N-phenyltriazolidinedione; and 1,4-benzoquinone and 2,3-diazo-1,4-benzoquinone and derivatives thereof in which the benzene ring carries one or more substituents. In other dienophiles, which are of somewhat lesser interest, the electron withdrawing grouping may instead contain a cyano group, a nitroso group or an ether group as, for example, in tetracyanoethylene, nitrosobenzene and alkoxy olefines such as vinyl methyl ether, respectively.

Other, less common forms of dienophile, which are however of particular interest in the context of the present invention, include compounds containing a sulphur atom joined by double bonds to one or particularly more electronegative atoms, for example two atoms such as oxygen atoms, and compounds containing a phosphorus atom joined to one or particularly more electronegative atoms, for example three atoms such as halogen atoms. Specific examples of such dienophiles are sulphur dioxide and phosphorus tribromide.

It will be appreciated that when the dienophile is of a type which contains two multiply bonded atoms, of which at least one carries as electron withdrawing group, then the dienophile residue A which is shown in formula (2) above will correspond to the dienophile but with the number of bonds between the two atoms reduced by one and with each atom instead possessing a free valency for bonding of the residue A into a six membered ring. With a dienophile of the type which contains an atom such as oxygen or phosphorus carrying a lone pair of electrons not involved in the attachment to these atoms of other, electronegative, atoms then the dienophile residue A will correspond to the dienophile but with these lone pair electrons providing the free valency for bonding of the residue A into a five membered ring.

As indicated above, the Diels-Alder adduct may not only be used directly in aphid control but may also in some cases first be converted to a derivative of the adduct before use. In such derivatives the dienophile residue A shown in formula (2) and/or the remainder of the ring containing A is modified by one, or where appropriate by a combination of two or more of the modifications (for example 2 and 3 or 2, 3 and 4) listed below, the compounds derivable by such modifications being included by the present invention.

1. Reduction of an alkoxycarbonyl group or groups to a methylol or methyl group.

2. Hydrolysis of one or more ester groups to a carboxy group (particularly groups —CO.O-alkyl), the product being isolated as the free acid or as a salt.

3. Decarboxylation with the replacement of one or more carboxyl groups of hydrogen. The groupings —N(CO$_2$H)—N(CO$_2$H)— and —N(CO$_2$ alkyl)—N(CO$_2$H)— will undergo spontaneous decarboxylation to give the groupings —NH—NH— and —N(CO$_2$ alkyl)—NH—, respectively. The grouping —NH—NH— may also undergo further spontaneous reaction, for example to —N=N— followed by ring cleavage, so that hydrolysis of only one or two vicinal N-alkoxycarbonyl groups is preferred in a reaction to produce a modification of type 2.

4. Oxidation either to introduce an additional separate double bond into the ring formed by the Diels-Alder reaction or to convert this ring to aromatic form. Such oxidation is preferably applied to carbocyclic rings, for example after following a reaction to produce a modification of type 3 in which two vicinally disposed carboxyl groups are decarboxylated. For the reasons indicated under 3 application of such an oxidation to N-heterocycles is more difficult, particularly when a reaction —N(CO$_2$H)—N(CO$_2$H)—→—NH—NH— is involved, but oxidation of both cyclohexene and cyclohexadiene ring systems to benzene, for example, is possible.

5. Modification of an alkoxycarbonyl group or groups to effect replacement thereof by a group $$-\overset{O}{\underset{\|}{C}}-S-T$$

in which S may be O or NR$^2$ and T may be NR$^2$R$^3$ or (when S is NR$^3$) may be OR$^2$, R$^2$ and R$^3$ each being separately selected from hydrogen, and alkyl and aryl groups, for example lower alkyl groups (i.e. of one to four carbon atoms) and phenyl.

6. Modification of a trihalophosphorus group to a group

in which R$_1$ represents an —O-alkyl or —S-alkyl group containing, for example, lower alkyl groups such as methyl or ethyl, and R$_2$ and R$_3$ together represent either a carbonyl or thiocarbonyl group, respectively.

Other modifications include:

7. Modification of the imino group of a grouping —CO—NH—CO— to replace the hydrogen atom of that group by a group —CO.OR wherein R is a monovalent aliphatic hydrocarbon group, for example an alkyl group and particularly a lower alkyl group such as methyl or ethyl or other groups R as discussed herein, optionally followed by replacement of the group —CO.OR by a group —D—CO.OR$^1$ in which D is a divalent aliphatic hydrocarbon group, for example of one to four carbon atoms, particularly an alkylene group such as methylene and R$^1$ is a salt forming cation, for example an alkali metal cation, hydrogen or a monovalent aliphatic hydrocarbon group, for example a group R such as described herein.

8. Modification of groups —CO.N(CO.OR).CO— produced directly as a Diels-Alder adduct to form a grouping —CO.N(D.CO.OR$^1$)CO— as described above.

9. Modification of an acid anhydride group,

to give the dicarboxy compound,

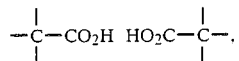

either as the free di-acid or preferably as a salt thereof, for example an alkali metal salt such as the di-sodium salt. Such a modification is applicable especially to the adduct from maleic anhydride.

In the following discussion of compounds according to the present invention it will be apparent from the nature of the group A, compare with formula (2), what dienophiles have been used to prepare the compounds and what further modifications of adducts have been effected according to the previous discussion.

One group of compounds according to the present invention which is of particular interest is represented by the formula

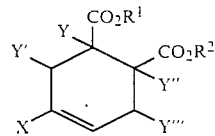

wherein X represents a 4,8-dimethyl-3,7-nonadienyl, Y, Y', Y" and Y'" each represent hydrogen or any two of these which are adjacent represent the second bond of a carbon-carbon double bond joining the positions to which they are attached and the other two represent hydrogen, or Y and Y' together and Y" and Y'" together each represent such a second bond of a carbon-carbon double bond, the ring being aromatic, and $R^1$ and $R^2$ each separately represent hydrogen or monovalent aliphatic hydrocarbon group.

One group of compounds according to the present invention which is of particular interest is represented by formula (3):

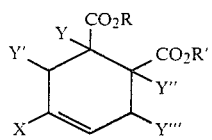
(3)

wherein X represents a 4,8-dimethyl-3,7-nonadienyl group, Y, Y', Y" and Y'" each represent hydrogen or any two of these which are adjacent represent the second bond of a carbon-carbon double bond joining the positions to which they are attached and the other two represent hydrogen or Y and Y' together and Y" and Y'" together each represent such a second bond of a carbon-carbon double bond, the ring being aromatic, and R and R' each separately represent an aliphatic hydrocarbon group.

In preferred compounds of formula (3) the ring is aromatic, or particularly all four groups Y, Y', Y", Y'" are hydrogen or, more especially, Y' and Y'" are hydrogen and Y and Y" represent the second bond of a carbon-carbon double bond. The groups R' and R" may each represent a different aliphatic hydrocarbon group but are most conveniently the same. The aliphatic hydrocarbon group may be branched or unbranched and saturated or unsaturated. The presence of a high degree of branching may lead to a reduction in activity but branching of the type which involves the carbon atom attached to the group —CO.O—, i.e. the ester group being derived from other than a primary alcohol and particularly a secondary alcohol, may be of value in conferring upon the compound a greater level of stability in the field. Similarly, whilst good levels of activity are obtainable with saturated aliphatic hydrocarbon groups (alkyl groups), the presence of unsaturation in R and R', for example one double bond i.e., alkenyl, may increase the dispersibility of the compound without any disadvantageous effect and may even lead to an improvement in activity.

The range of size of the aliphatic hydrocarbon groups R (and R') can be quite considerable ranging from 1 up to 18 or 20, or even as high as 28 or 30, depending on whether the chain is branched and/or unsaturated, and on the exact nature of the activity against aphids which the compound is required to exhibit. When R and R' are selected from unbranched alkyl groups a range of size of $C_8$ to $C_{16}$ may conveniently be used to produce compounds of formula (3) effective in preventing the settling of aphids. Above this range the activity tends to change to an arrestant one causing aggregation rather than repulsion of the aphids, although such activity may itself be of value as discussed hereinafter. A preferred range within that of $C_8$–$C_{16}$ is $C_8$–$C_{14}$ or $C_8$–$C_{12}$, compounds in which R and R' are each unbranched alkyl groups of 9, 10 or 11 carbon atoms being of particular interest, the level of repellent activity generally increasing from 9 to 10 and from 10 to 11 carbon atoms, and then falling thereafter. When R and R' are selected from unsaturated aliphatic hydrocarbon groups, settling prevention activity may be maintained up to higher carbon values so that, for example, the compound having R=R'=oleyl is of higher repellent activity than that in which R=R'=octadecyl, showing dispersant rather than arrestant activity. However, although some difference as to preferences within the broad range of carbon size may occur as to whether R is saturated, unsaturated, straight chain or branched, the preferences indicated above for straight chain alkyl groups may often be generally applied.

Specific examples of groups from which R and R' may be selected are octyl, nonyl, decyl, undecyl, dodecyl, tridecyl, tetradecyl, pentadecyl, hexadecyl, heptadecyl, octadecyl, oleyl, 1-methyldecyl, 1-methylnonyl, 1-methyloctyl, 5-decenyl, 10-undecenyl, 5-undecenyl, and 6-undecenyl.

The comments made above in relation to the groups R and R' in compounds of formula (3) apply generally to compounds of formulae (4) and (5) which are also of some interest:

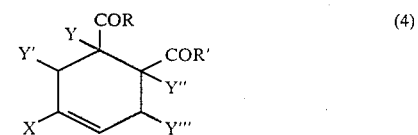
(4)

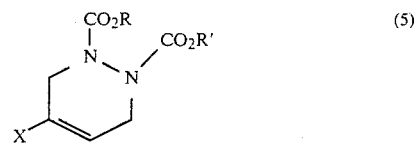
(5)

the symbols R, R', Y, Y", Y', Y'" and X having the meanings indicated above. In the case of compounds of formula (4) a compound having a group COR with R containing a particular number of carbon atoms may show properties more closely related to the compound formula (3) having a group CO.OR with R of one less carbon atom, the group being of closely similar size due to the presence of the extra oxygen atom. As indicated above, however, the broad preferences mentioned generally apply.

Other diester compounds include compounds of formula (6) and (7):

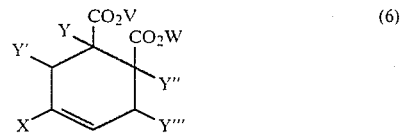
(6)

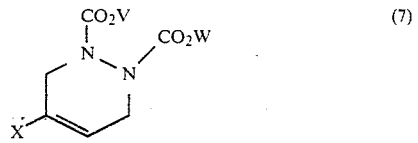
(7)

wherein X, Y, Y', Y" and Y'" are as defined above, V represents a group —$(CH_2CH_2O)_nH$ in which n is an integer conveniently from 1 to 9 or 10 and preferably 1 to 5 or 6, and W represents the same or different group —(CH₂CH₂O)ₙ'H or a group R as defined above. Preferred compounds have groups Y, Y', Y" and Y''' as discussed above, groups V and W which are each —(CH₂CH₂O)ₙ'H and conveniently the same group of this type, and values of n of 2, 3 or 4. Compounds of formula (6) are of greater interest than those of formula (7).

Another group of compounds of especial interest are those of formula (6):

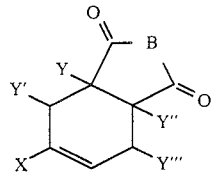
(8)

wherein X Y, Y', Y" and Y''' are as above, B is —O—, —NH— or >N—D—CO₂R¹ in which D represents a direct bond between the nitrogen atom and the group CO₂R or a divalent aliphatic hydrocarbon group, and R¹ represents hydrogen, a salt cation or a group R as above. The interest in these compounds resides particularly in the fact that they may exhibit at least some degree of systemic activity. Among these compounds B is preferably oxygen or especially a group >N—D—CO₂R¹, particularly when D is of one to four carbon atoms, for example methylene, and/or when R¹ is hydrogen or a salt cation, and Y, Y', Y" and Y''' are preferably each hydrogen.

A range of specific examples of compounds per se which are included within the scope of the present invention is shown below, the linear part of the residue of (E)-β-farnesene [an (E)-4,8-dimethyl-3,7-nonadienyl group] being shown in full in the first formula and by the symbol X thereinafter, n representing an integer from 1 to 18, particularly 9, 10 or 11 in the first two formulae and 10, 11 or 12 in the seventh formulae, and n' representing an integer from 1 to 10, particularly 2, 3 or 4.

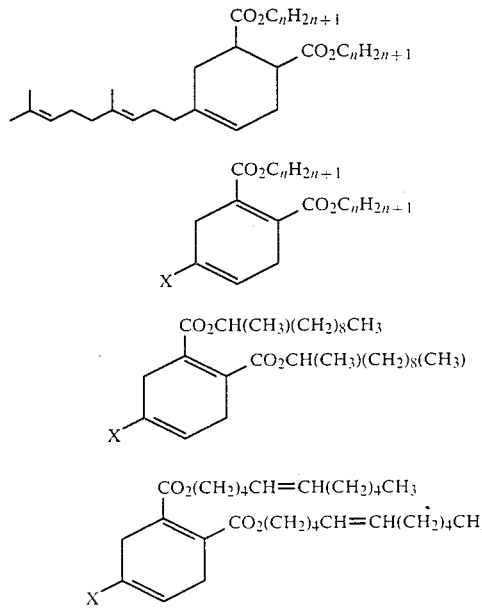

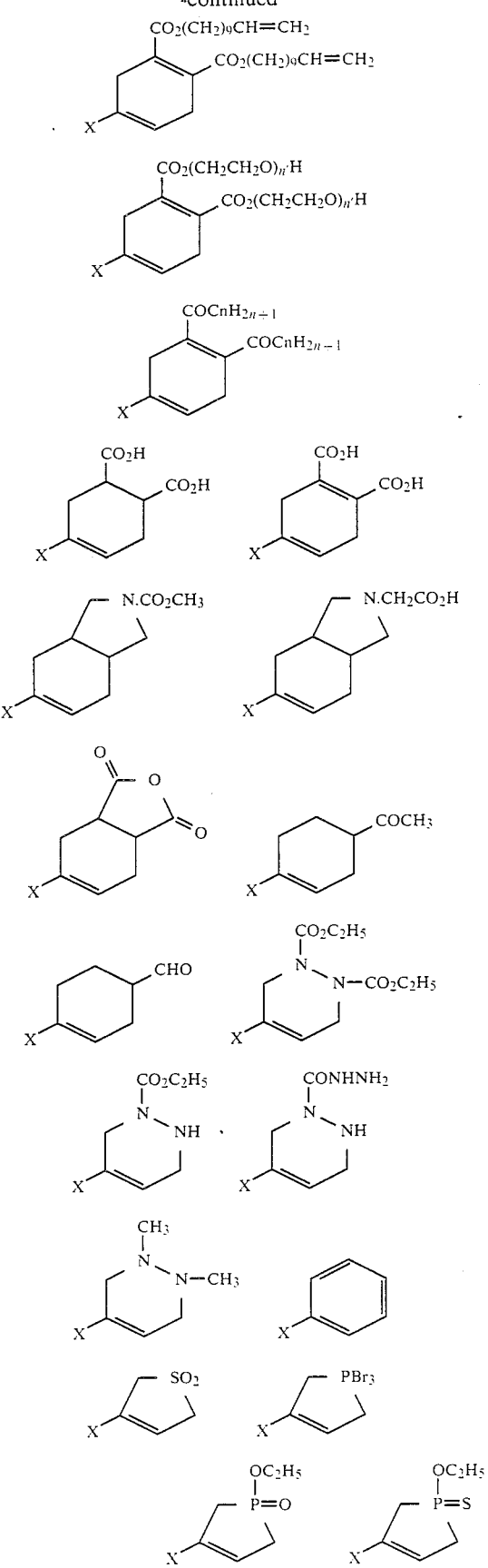

(E)-β-farnesene provides a convenient starting material for the preparation of the compounds according to the present invention. A preferred route to (E)-β-farnesene is the dehydration of (E)-nerolidol (9) or of (E,E) or (Z,E)-farnesol (10):

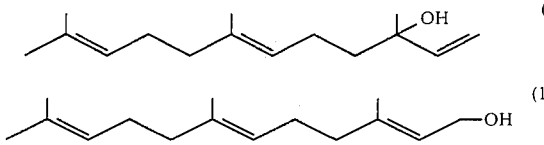

However, the procedures which have previously been described in the art for effecting dehydration, such as the use of phosphorus oxychloride/pyridine with (E)-nerolidol and potassium hydroxide with (E,E)- and (Z,E)-farnesol have varous disadvantages such as low yields coupled with difficulties in large scale operation, and considerable contamination with alternative dehydration products so that in the case of nerolidol, for example, a high proportion of α-farnesenes often results on dehydration. These problems are compounded by the fact that the commercially available forms of nerolidol and farnesol are mixtures of isomers, i.e. (E)- and (Z)-nerolidol and (Z,Z)-, (Z,E)-, (E,Z)- and (E,E)-farnesol, only certain of which are capable of yielding the desired (E)-β-farnesene on dehydration. We have therefore turned our attention to this problem and have discovered a new process for the production of (E)-β-farnesene which is superior to the processes described in the liturature.

According to the present invention a process for the production of (E)-β-farnesene from (E)-nerolidol comprises passing (E)-nerolidol through heated aluminium oxide.

Whilst it is possible to apply the process to purified (E)-nerolidol, it is more convenient in practice to use commercially available nerolidol containing a mixture of (E)- and (Z)-nerolidol as the starting material and the process of the present invention is sufficiently successful for the resulting contamination with (Z)-β-farnesene to be acceptable since the dehydration product obtained contains a relatively low proportion of isomeric hydrocarbon contaminants, very little of the α-farnesenes being produced. The yield of β-farnesenes which can be obtained from commercial nerolidol by the process of the present invention typically lies in a range from 40% to 70% with a proportion of the (E) isomer to the (Z) isomer in the mixture which is typically about 2:1.

In order to obtain yields of the level just quoted, the aluminium oxide (alumina) used should be substantially free of active acidic sites. The yields obtained with commercial neutral alumina are thus only very low and whilst commercially available basic alumina may be employed, it has been found that enhanced yields result from using commercially available alumina, particularly neutral alumina, and exposing this before use to a base, particularly a nitrogenous base such as ammonia or especially an organic base including mono, secondary and particularly tertiary amines. The bases which may be used include linear aliphatic bases such as triethylamine or analogues thereof containing three, similar or different, alkyl groups (e.g. lower alkyl groups) cyclic aliphatic bases such as cyclohexylamine, carbocyclic aromatic bases such as aniline, and both non-aromatic and aromatic heterocyclic bases such as pyrrolidine and pyridine.

The present invention thus includes a process for the production of (E)-β-farnesene from (E)-nerolidol which comprises passing (E)-nerolidol through heated aluminium oxide treated with a nitrogenous base.

The passage of the nerolidol through a mass of alumina means that the nerolidol and particularly the farnesene produced therefrom is in contact with the alumina for only a relatively short period, the residence time perhaps being of the order of only about one minute, as compared with the more conventional type of reaction carried out in a vessel in which reactants and products are maintained together for some time. It is believed that the rapid completion of the reaction followed by the rapid removal of the volatile farnesene from the reaction site may be responsible for the high yields which may be obtained.

Conveniently the nerolidol is passed through a heated column of alumina, for example by the application of a vacuum or the use of a stream of inert gas such as nitrogen. Alternatively the nerolidol may be allowed to drip on to the hot alumina in such a column which is maintained under vacuum. In the preferred procedure which uses a base to treat neutral alumina, the base is conveniently passed through the column just prior to its use for the dehydration, conveniently again employing vacuum or an inert gas stream. The alumina may conveniently already be at an elevated temperature when treated with the base, for example the same temperature as is used for the dehydration. This temperature is selected in order to avoid pyrolysis and cyclization resulting from the use of too high a temperature and to avoid lack of reaction or loss of yield resulting from too low a temperature. The dehydration is preferably carried out using a temperature in the range from 125° to 350° C., conveniently 180° to 220° C., for example about 200° C. Preferably the nerolidol is in the vapour state and may conveniently be contacted with the heated alumina under a vacuum which enables the nerolidol to be vaporised at a lower temperature than otherwise, a convenient vacuum being 10τ or less, particularly 1τ or less, for example 0.1 to 0.2τ.

The product from the dehydration may conveniently be purified by chromatography on an adsorbent such as silica gel with a hydrocarbon solvent such as hexane as an eluant to remove any oxygen-containing impurities or alternatively may be used directly. Although chromatography, for example on silver nitrate, may be used to remove the (Z)-isomer and other, minor, isomeric hydrocarbon impurities from the (EI)-β-farnesene, it is preferred in practice to use the (E), (Z) mixture as such. (E)-β-farnesene is susceptible to aerial oxidation (particularly as the product produced according to the present invention is substantially free of α-farnesenes) and if storage under nitrogen is not used then even at −20° C. in the dark oxidation will cause a 20% loss of activity after seven days storage. Accordingly, the compound is preferably stored under nitrogen in sealed ampoules and in use is then generally as active as the natural pheromone allowing for the percentage of the active ingredient (E)-β-farnesene which it contains.

Preparation of (E)-β-farnesene derivatives according to the present invention conveniently involves reaction of (E)-β-farnesene with the particular dienophile under conditions similar to those described in the literature for the reaction of that dienophile with other dienes such as buta-1,3-diene, etc. Diels-Alder reactions generally require a variety of conditions ranging from simple admixture at room temperature to heating at sometimes quite elevated temperatures. As would be expected, the Diels-Alder reaction of (E)-β-farnesene proceeds more readily with some dienophiles than others, examples of dienophiles which are more difficult to react including tetracyanoethylene, 1,4-benzoquinones and alkoxy olefines. In such cases, techniques known in the art for use in connection with difficult Diels-Alder reactions may be employed such as the use of Lewis acids, for example boron trifluoride, with alkoxyolefines such as vinyl methyl ketone.

Accordingly the present invention also includes a method for preparing (E)-β-farnesene derivatives as described hereinbefore which comprises treating (E)-β-farnesene with a dienophile to effect a Diels-Alder reaction between these reactants with the formation of a Diels-Alder adduct which may optionally be modified by further reaction as described hereinbefore.

Where the desired derivative involves modification of a Diels-Alder adduct, appropriate conditions are used to effect the modification. Thus, referring to the modifications listed hereinbefore the following types of reaction may be employed in the various cases.

1. The reactions $>$N—CO$_2$alkyl→$>$N—CH$_3$ and

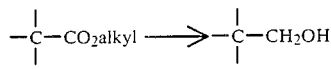

may conveniently be effected using a metal hydride reagent such as lithium aluminium hydride.

2. Hydrolysis may conveniently be effected using an alkali metal hydroxide such as potassium hydroxide, for example in an aqueous alcoholic medium such as aqueous ethanol. The product may then be isolated directly as carboxylate salt or, where desired, treatment with acid is used to allow isolation of the product as the free acid (or even by subsequent treatment with base as another type of salt).

3. Decarboxylation may conveniently be effected on standing at ambient temperature for compounds in which the carboxylic acid group is attached to nitrogen or by heating an appropriate salt of the acid if this group is attached to carbon.

4. Mild oxidation may conveniently be effected by treatement with an oxidizing agent such as mercuric oxide or ferric chloride and stronger oxidation with other selected oxidizing agents such as selenium, for example for the aromatization of dihydro- and tetrahydrobenzenes.

5. The modification

wherein S and T are as hereinbefore defined, may conveniently be effected by reaction with a compound H—S—T. Thus, for example the reaction —CO$_2$alkyl→—CONHNHR$^2$ employs hydrazine when R$^2$=H or a substituted hydrazine NH$_2$NHR$^2$ in other cases.

6. The modification

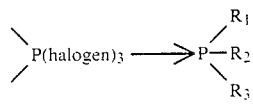

may conveniently be effected by a reaction with an alcohol or mercaptan containing the desired alkyl group which is present in the group R$_1$. Thus, for example the reaction

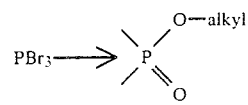

employs an alcohol (alkyl—OH) as the reagent whilst the reaction

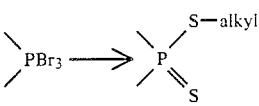

employs a mercaptan (alkyl-SH) as the reagent. Reactions of this general type are well known in the literature, the conditions involving reaction of the two reagents in the presence of a base, such as pyridine, in the cold or with heating as necessary.

7. The modification —CO.NH.CO→—CO.N-(CO$_2$R).CO→—CO.N(D—CO$_2$R$^1$).CO— may conveniently be effected by reacting the maleimide, or like adduct, with an ester of chloroformic acid, particularly the ethyl or especially the methyl ester in a procedure well known in the art for effecting substitution by an ester group, followed where desired by reaction with an amino acid, for example glycine and preferably in aqueous sodium bicarbonate as a reaction medium, to effect replacement of the ester group by the residue of the acid lacking the amino group, again in a procedure well known in the art for effecting this type of reaction.

8. Alternatively the intermediate type of modification containing an ester group may also be produced directly, for example by formation of the Diels-Alder adduct with N-methoxycarbonylmaleimide, and the compound so prepared may then be modified further by reaction with an amino acid as described above.

9. The modification

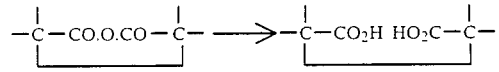

may conveniently be effected by treatment with an aqueous base, for example aqueous sodium hydroxide, the product being isolated as the free di-acid or as a salt.

It will be appreciated that the reactions described above are not the only ones which may be used for effecting the modifications to the Diels-Alder adducts and that various alternative reaction procedures may be used as will be apparent from the art relating to reactions of the same general type.

The various Diels-Alder adducts according to the present invention will generally, excepted as discussed hereinafter, infuence the distribution of aphids on plants in a similar fashion to (E)-β-farnesene. It is not certain at the present time whether this activity arises from a release of (E)-β-farnesene in the field, from the retention of the activity of the parent compound in the derivatives themselves or from another cause. It is believed, however, that the primary cause of activity may depend on the particular type of Diels-Alder adduct. Thus with certain compounds the primary cause of activity may arise from the occurrence of a reverse 1,4-cyclo-addition reaction or retro Diels-Alder reaction, for example:

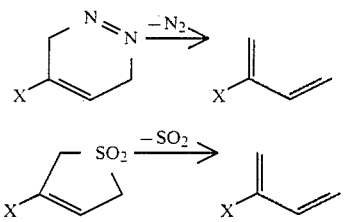

it is believed that the former, N-heterocyclic, system may be generated under field conditions from various related N-substituted systems. With other compounds, such as the adducts with maleic anhydride, diethyl maleate and diethyl acetylene 1,2-dicarboxylic acid, the primary cause of activity may well result from the activity of the compound as such. A particular advantage of the present invention lies in the variety of Diels-Alder adducts which may be prepared from (E)-β-farnesene, thus enabling a compound having the best properties for a particular situation, in terms of solubility and compatibility with plants or other pest control agents, etc., to be selected. Among the adducts described hereinbefore derivatives capable of generating a 3,6-dihydropyridazine structure or especially derivatives having a sulpholene structure are preferred when release of (E)-β-farnesene as such is desirable but, where this is not necessarily required, the adducts with diethyl maleate and diethyl acetylene 1,2-dicarboxylate and related compounds are of particular value.

The alarm activity of (E)-β-farnesene and of the derivatives of the present invention is effective for many aphid species, for example *Myzus persicae* (Sulz.) although there are some species where little activity is shown, for example *Brevicoryne brassicae*(L.), *Aphis sambuci*(L.) and *Hyalopterus pruni*(Geoffroy). Aphid control is required in relation to a wide variety of crops including Angiosperms, Gymnosperms, etc. The present invention is thus applicable to arable, orchard and horticultural crops including particularly beet, potatoes, cereals such as wheat and barley, beans, hops, cotton and various fruit crops. The derivatives may be formulated in various ways, depending on the particular use as discussed hereinafter, usually by conventional procedures. However, they are often applied together with some form of diluent or carrier. The present invention thus includes a pest control composition comprising an (E)-β-farnesene derivative which is obtainable as a Diels-Alder adduct of (E)-β-farnesene and a dienophile or by modification of such an adduct in a manner as defined hereinbefore together with a diluent or carrier.

Various types of diluents or carriers suitable for agricultural applications, particularly to plants, may be used including aqueous formulations, oily formulations, etc. One type of formulation of particular interest is as an emulsion in water which may, if desired, employ emulsifying agents, particularly non-ionic surface active agents and especially those based on a polyether structure, for example polyoxyethylene stearate and nonyl phenylpolyoxyethylanol. An alternative type of formulation is microencapsulation, for example in a polyurea capsule, since the derivatives, although more stable than (E)-β-farnesene itself, may benefit from some protection against aerial oxidation, particularly in certain of their uses described hereinafter. For this reason, it may also be worthwhile including an antioxidant, for example an N-phenyl-N'-alkyl-p-phenylenediamine or B.H.T. in microencapsulated or other formulations. I will be appreciated, however, that ultra low volume techniques may enable one to reduce or even dispense with the use of a diluent or carrier.

One of the main areas of use of compounds according to the present invention in pest control involves their use as an aphid dispersant in conjunction with a pesticidal (aphicidal) spray in order to increase contact of the aphid with the toxicant through the increased movement of the aphids on the crop. Such a procedure most usually involves application, to a crop on which aphids are present or which they may be expected to infest, of the (E)-β-farnesene derivative followed shortly thereafter by a pesticide composition. A wide variety of pesticides may be used including particularly pyrethroid pesticides, for example permethrin, organophosphorus pesticides, for example malathion, or fenitrothion and some carbamates, for example carbaryl, etc. In order to be advantageously used in conjunction with the derivatives the pesticide will usually be required to have some degree of contact action. Thus, the systemic activity of pesticides or the translaminar or fumigant action of compounds such as pirimicarb, will not normally be enhanced by the use of repellant or dispersant derivatives. Only in the exceptional case of derivatives such as the Diels-Alder adduct between (E)-β-farnesene and di-octadecyl acetylene dicarboxylate which show arrestant activity may this activity be utilised in increasing contact between aphids and a systemic pesticide with which a crop has been treated. The action of pesticides having both systemic and contact activity, for example dimethoate, should be improved by the use of the majority of compounds according to the present invention which have a dispersant action. Indeed, the enhancement of the contact action of pesticides which is produced by the use of dispersant compounds may enable the use of contact pesticides which are not normally sufficiently active for use as aphicides. Such dispersant compounds may also enhance the action of other pest control agents such as adhesives, hormones and biological agents including viruses, bacteria, parasitoids, parasites and predators. This has the advantage of bringing into use pesticides and other agents to which aphids have not the opportunity to develop any significant level of resistance as they have to some of the commonly used systemic aphicides.

The period between application of the derivative and the pesticide can be quite short, not normally being longer than about 15 minutes, and one convenient mode of application involves the use of a tractor with a boom at the front which dispenses the derivative and one at the back which dispenses the pesticide composition. Providing the two are compatible it is also possible to apply the derivative and pesticide mixed in a single composition.

Accordingly the present invention further comprises a method of aphid control which comprises applying to a crop an (E)-β-farnesene derivative as described hereinbefore in conjunction with a pesticide.

It is even possible to combine (E)-β-farnesene activity and pesticidal activity in one compound, for example in the organophosphorus compounds of the form.

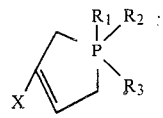

wherein X, R₁, R₂, R₃ are as defined hereinbefore. Such compounds may be employed in the pesticidal control of aphids either with or without the associated use of a separate pesticide.

Since the particular use just described of the (E)-β-farnesene derivatives in aphid control utilises the activity of the derivative quite rapidly after it is applied, stability considerations are not quite as important as in the other main areas of use described hereinafter. It is possible, therefore, in this usage to consider the use of (E)-β-farnesene itself, most conveniently dispensed as a vapour in a stream of nitrogen or air. A suitable rate of application is conveniently about 5 to 1000 mm/second, for example about 230 mm/second. The present invention thus extends to the use of (E)-β-farnesene prepared as described hereinbefore in aphid control as well as to provide a starting material for the preparation of derivatives according to the present invention.

A further main area of use of (E)-β-farnesene derivatives according to the present invention involves their use in the control of aphid behaviour per se as opposed to when associated with their destruction. Since this use, unlike that just described, requires activity to be sustained over an extended period, the derivatives of the present invention are much more suited to it than (E)-β-farnesene itself and it represents the most important aspect of the use of these derivatives in aphid control. The settling and larviposition of aphids on plants leads to damage of those plants through (a) feeding, (b) moulds growing on the honey dew formed by aphids, and (c) injection of xenobiotics from aphid saliva during feeding and sampling which causes distorted plant growth, etc., and the application to plants of the derivatives will control or prevent such damage. A further area of use of the derivatives in the control of crop damage lies in the control of virus transmission by aphids. Apart from the type of damage described above caused by aphids settling on crops, the feeding, and the sampling by the insects which precedes feeding, also produce crop damage by encouraging the spread of any virus infection present within the crop. Thus, for example, the semi-persistent beet yellow virus and the non-persistent potato virus Y are normally acquired very rapidly by aphids such as *Myzus persicae* and transmitted by them. Application of the derivatives to plants through influencing aphid behaviour as described above will also prevent or control such transmission and represents a very important use of the present invention.

Accordingly the present invention further comprises a method for the control of crop damage by aphids which comprises applying to a crop an (E)-β-farnesene derivative as described hereinbefore. It will be appreciated that, if desired, the derivatives may be administered in admixture with or in conjunction with other crop damage control agents including certain pyrethroids that control virus transmission by aphids, or indeed with any other types of agricultural agent with which their use can conveniently be combined.

Treatment of a crop with an (E)-β-farnesene derivative according to the present invention is of value for the control of crop damage which it will achieve. However, where the derivative is one such as is discussed above which also shows aphid toxicity, for example an organo phosphorus compound, then control is exerted in two ways, i.e. both through control of damaging aphid activity and through aphid destruction. With those derivatives not possessing a toxic action in their own right it is preferred, whilst applying the derivative to the crop, to take the opportunity of also applying a pesticide either concomitantly with or immediately after the derivative. Whilst, as indicated above, such a pesticide preferably has some contact action, it is of course possible to apply a systemic pesticide whilst applying the derivative although the latter will, unless one of the attractant compounds according to the present invention is employed, then function substantially only through control of crop damage rather than also through enhancement of the effect of the pesticide.

The (E)-β-farnesene derivatives of the present invention may be applied to crops using standard techniques or newly developed methods. Application may be made before or following infestation of the crop. Electrostatic spraying is one existing technique which is of particular interest for the application of the derivatives to crops. Thus, aphids often feed on the lower surfaces of leaves and electrostatic spraying will achieve improved coverage of such parts of the plant. With many of the compounds of the present invention only a contact effect is present so that good coverage of the plant is important. With certain compounds, however, and particularly those of formula (8) a level of systemic activity may also be present so that the compound is translocated through a plant to areas other than those directly contacted by the compound. Whilst crop application levels will depend on the particular derivative used and on the particular use being made of it, it may be stated as a guide that a rate of application to crops from about 10 mg to 1 kg/ha, conveniently 100 mg to 100 g/ha, for example 300 mg/ha is often suitable. These rates are applicable whether the derivative is applied alone or with a pesticide. The pesticides may conveniently be applied at conventional dosage rates.

The (E)-β-farnesene derivatives of the present invention, in view of their structural similarities to the juvenile hormones, are also of interest for the control of pests other than aphids, particularly other insects such as the holometabolous insects. Broadly similar techniques may then conveniently be used to those described above in relation to aphid control. Moreover, it is possible that the compounds may exert beneficial effects in pest control and over the virus infection of plants through mechanisms additional to those specifically discussed above.

The invention is illustrated by the following examples.

It will be seen that the various Diels-Alder adducts are prepared from (E)-β-farnesene which is in admixture with a minor amount of (Z)-β-farnesene. The various active adducts containing an (E)-(4,8-dimethyl-3,7-nonadienyl) group are the therefore obtained in admixture with the corresponding adduct containing (Z)-(4,8-dimethyl-3,7-nonadienyl) group having the cis rather than the trans configuration about the double bond joining the 3 and 4 positions. It will be appreciated that either such cis compounds are an inactive but quite acceptable contaminant of the trans compounds or, as indicated above, contribute some worthwhile activity to the mixture.

EXAMPLES

Example 1

Preparation of (E)-$\beta$-farnesene

The preparation is carried out using glass Quickfit type apparatus comprising a column having a sinter at the base thereof and which is surrounded by a heating coil. At the top of the main column is arranged a dropping funnel with a bypass tube and above this funnel is a small column on top of which is fitted a vacuum gauge and at the side of which is a downwardly pointing tapped take off terminating in a small round bottomed flask. At the bottom of the main column is an air cooled trap having a take off to a pump. Neutral alumina (50 g) is placed in the main column and is heated to 200° C. under a vacuum (0.1–0.2$\tau$) provided by a rotary pump. Pyridine (4 g) from the round bottomed flask is allowed to evaporate and pass through the bypass tube and then through the column. Nerolidol (80 g, commercial material containing (E) and (Z) isomers) is then allowed to drip from the dropping funnel into the column during a period of 4.5 hours. The product which is collected as a light brown liquid (69.5 g) in the air cooled trap below the column is chromatographed on Florisil (200 g) with hexane. Removal of the hexane under vacuum gives a straw coloured liquid (68.7 g, containing 67% of theoretical yield of $\beta$-farnesenes), which consists predominantly of a mixture of (E)- and (Z)-$\beta$-farnesene and contains 47% w/w of (E)-$\beta$-farnesene and 23% w/w of (Z)-$\beta$-farnesene. The final product is sealed under nitrogen in batches (10 mg and 1 g) in glass ampoules.

Example 2

Preparation of Diels-Alder adduct between (E)-$\beta$-farnesene and diethyl azodicarboxylate (I)

A solution of the (E)-$\beta$-farnesene-containing product of Example 1 (14.5 g) in ether (20 ml) is cooled to −20° C. and diethyl azodicarboxylate (8.7 g) is slowly added with stirring. The mixture is stored at −20° C. overnight and then at 4° C., the reaction being shown by n.m.r. to be complete after 8 hours at 4° C. The mixture is then subjected to fractional distillation to give the adduct, 1,2-bis(ethoxycarbonyl)-4-(4,8-dimethyl-3,7-nonadienyl)-1,2,3,6-tetrahydropyridazine (I) as a yellow oil (8 g, 43%) 180°–185° C./0.3$\tau$; $n_D^{20}$ 1.4938; M+ (m/z as % of base peak): 378(2.9); $\delta$(CCl4) 1.30 (t, 6H), 1.70 (m, 9H), 2.08 (m, 8H), 3.60–4.40 (m, 4H), 4.26 (q, 4H), 5.20 (m, 2H), 5.60 (br, t, 1H).

Example 3

Preparation of Diels-Alder adduct between (E)-$\beta$-farnesene and sulphur dioxide (II)

The (E)-$\beta$-farnesene containing product of Example 1 (17 g) and liquid sulphur dioxide are sealed in a glass ampoule and stored at ambient temperature for 18 hours. The ampoule is opened after cooling and the excess SO$_2$ is allowed to evaporate. The residue is then chromatographed on Florisil using sequentially hexane, an ether/hexane mixture of increasing concentration in ether, and finally ether, the effluent being monitored by n.m.r. Removal of the solvent under vacuum from the appropriate fractions gives 3-(4,8-dimethyl-3,7-nonadienyl) sulpholene (II) as a straw coloured liquid (9 g, 58%); $n_D^{20}$ 1.5080; M+ (m/z as % of base peak): 26 (0.02); $\delta$(CCl4) 1.70 (m, 9H), 2.08 (m, 8H), 3.70 (m, 4H) 5.16 (m, 2H), 5.78 (br, t, 1H). Note: On heating at 180 C. under a vacuum of 1$\tau$ the sulpholene regenerates a (E)- and (Z)-$\beta$-farnesene mixture in high yield.

Example 4

Preparation of 1-ethoxycarbonyl-4-(4,8-dimethyl-3,7-nonadienyl)-1,2,3,6-tetrahydropyridazine (III)

The Diels-Alder adduct of Example 2 (4.0 g) is hydrolysed by placing it in a solution of potassium hydroxide (5.0 g) in water (5.0 g) and ethanol (25.0 ml) for days at room temperature. The resulting solution is partitioned with water (25 ml) and light petroleum (60°/80°; 25 ml) and the aqueous phase is acidified with acetic acid and partitioned with light petroleum (60°/80°; 25 ml). The light petroleum solution is dried (MgSO4) and then concentrated to give the title compound (III) as a yellow oil (2.5 g, 77%); $n_D^{20}$ 1.5022 M+ (m/z as % of base peak): 306 (38.6); $\delta$(CCl4) 1.30 (t, 3H), 1.70 (m, 9H), 2.08 (m, 8H), 3.40 (m, 2H, 3.96 (br, 2H), 4.22 (q, 2H), 4.30 (br, t, 1H), 5.20 (m, 2H), 5.60 (br, t, 1H).

Example 5

Preparation of 1,2-bis-methyl-4-(4,8-dimethyl-3,7-nonadienyl)-1,2,3,6-tetrahydropyridazine (IV)

The Diels-Alder adduct of Example 2 (5.0 g) is added slowly to a stirred suspension of lithium aluminium hydride (1.5 g) in dry ether (100 ml) and the mixture then refluxed for a further 0.5 hours. The excess hydride is destroyed by adding ethyl acetate and a granular precipitate is formed by adding, in turn, water (1.5 ml) 2N NaOH (1.5 ml) and water (4.5 ml). The precipitate is filtered off and the filtrate concentrated and distilled to give title compound (IV) as a yellow oil (3.1 g, 77%) b.p. 130°–5° C./0.3; $n_D^{20}$ 1.5034; M+ (m/z as % of base peak): 262 (100); $\delta$(CCl4) 1.70 (m, 9H), 2.08 (m, 8H) 2.34 (s, 6H), 3.10 (m, 4H), 5.20 (m, 2H), 5.47 (br, t, 1H)

Example 6

Preparation of Diels-Alder adduct between (E)-$\beta$-farnesene and maleic anhydride (V)

The (E)-$\beta$-farnesene-containing product of Example 1 (6.0 g) and maleic anhydride (2.0 g) in carbon tetrachloride (20 ml) are reacted together at 25° C. for 2 hours. The mixture is then distilled under reduced pressure to give 4-(4,8-dimethyl-3,7-nonadienyl) cyclohex-4-ene-1,2-dioic anhydride as a yellow oil (3.5, 70% b.p.176°–182° C./0.25$\tau$; $n_D^{20}$ 1.5907; M+ (m/z as % base peak): 302 (2.3): $\delta$(CCl4) 1.70 (m, 9H), 2.08 (m, 8H 2.20–2.70 (m, 4H), 3.36 (m, 2H), 5.16 (m, 2H), 5.70 (br t, 1H).

Example 7

Preparation of Diels-Alder adduct between (E)-$\beta$-farnesene and acrolein (VI)

The (E)-$\beta$-farnesene-containing product of Example 1 (5.0 g) and acrolein (3.0 g) are heated together at 100 C. for two hours. The mixture is then distilled under reduced pressure to give 1-formyl-4-(4,8-dimethyl-3,7 nonadienyl)-cyclohex-4-ene as a yellow oil (2.2 g, 50%) b.p. 140°–150°/0.5$\tau$; $n_D^{20}$ 1.5033; M+ (m/z as % base peak): 260 (3.6); δ (CCl₄) 1.70 (M, 9H), 1.90–2.30 (m, 15H), 5.16 (m, 2H), 5.50 (br, t, 1H), 9.84 (br, s, 1H).

Example 8

Preparation of Diels-Alder adduct between (E)-β-farnesene and methyl ethenyl ketone (VII)

The (E)-β-farnesene-containing product of Example 1 (6.0 g) and methyl ethynyl ketone (1.5 g) are heated together at 150° C. for 16 hours. The mixture is then distilled under reduced pressure to give 1-acetyl-4-(4,8-dimethyl-3,7-nonadienyl)-cyclohex-4-ene as a pale yellow oil (2.3 g, 50%); b.p. 130°–140° C./0.2τ, $n_D^{20}$ 1.4998; M⁺ (m/z as % of base peak): 274 (3.0; δ(CCl₄) 1.70 (m, 9H), 2.00–2.80 (m, 15H), 2.22 (s, 3H), 5.20 (m, 2H), 5.50 (br, t, 1H).

Example 9

Preparation of Diels-Alder adduct between (E)-β-farnesene and diethyl maleate (VIII)

The (E)-β-farnesene-containing product of Example 1 (10 g) and diethyl maleate (5.0 g) are heated together at 180° C. for two hours. The mixture is then distilled under reduced pressure to give 1,2-bis-(ethoxycarbonyl)-4-(4,8 dimethyl-3,7-nonadienyl) cyclohex-4-ene as a pale yellow oil (8.5 g, 75%); b.p. 175°–180° C./0.3τ; $n_D^{20}$ 1.4894; M⁺ (m/z as % of base peak): 376 (6.6); δ(CCl₄) 1.24 (t, 6H), 1.70 (m, 9H), 2.08 (m, 8H), 2.36 (m, 4H), 2.80 (m, 2H), 4.14 (q, 4H), 5.20 (m, 2H), 5.40 (br, t, 1H).

Example 10

Preparation of Diels-Alder adduct between (E)-β-farnesene and didecyl ester of acetylene carboxylic acid (IX)

The (E)-β-farnesene-containing product of Example 1 (3.0 g) and the didecyl ester of acetylene dicarboxylic acid (4.0 g) are heated together at 80° C. for two hours. The mixture is then chromatographed on Florisil (100 g), eluting with increasing concentrations of ether in hexane, to give 1,2-bis(decyloxycarbonyl)-4-(4,8-dimethyl-3,7-nonadienyl)-cyclohexa-1,4-diene as a pale yellow oil (6.3 g, 62%); $n_D^{20}$ 1.4877; M⁺ (m/z as % of base peak): 598 (3.0); δ(CCl₄) 0.92 (t, 6H), 1.30 (m, 32H), 1.70 (m, 9H), 2.08 (m, 8H), 3.00 (m, 4H), 4.23 (q, 4H), 5.20 (m, 2H), 5.53 (br, t, 1H).

Example 1

Preparation of further Diels-Alder adducts between (E)-β-farnesene and other maleic acid and acetylene dicarboxylic acid diesters (E)-β-farnesene is reacted with various diesters of maleic acid and acetylene dicarboxylic acid (obtained commercially or prepared by standard esterification procedures from the appropriate acid and alcohol, for example by heating together and removing the water continuously as it is formed) in an analogous fashion to that described in Examples 9 and 10, respectively, using a reaction temperature of 180° C. and a time of 2 hours for the maleic acid esters and of 80°–90° C. and 2 hours for the acetylene dicarboxylic acid esters. Compound X is distilled but the other compounds are purified by chromatography as in Example 10.

Data relating to the various compounds of formula (11) are shown in Table 1 below, the values for compounds VIII and IX also being included for completeness [all of the compounds possess n.m.r. spectra in keeping with their structure (11)].

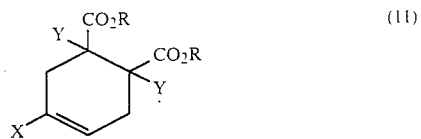

(X is a 4,8-dimethyl-3,7-nonadienyl group, Y and Y" represent hydrogen in compounds VIII and XIII and the second bond of a carbon-carbon double bond joining the positions to which they are attached in all of the other compounds, and R is as shown in Table 1).

TABLE 1

| COMPOUND | | Yield of purified compound as % of theoretical | Refractive index |
|---|---|---|---|
| No. | R | | |
| —VIII | —CH₂CH₃ | 75 | 1.4894 |
| X | —CH₂CH₃ | 60 | 1.5012 |
| XI | —(CH₂)₇CH₃ | 46 | 1.4854 |
| XII | —(CH₂)₈CH₃ | 56 | 1.4801 |
| —XIII | —(CH₂)₉CH₃ | 46 | 1.4800 |
| IX | —(CH₂)₉CH₃ | 62 | 1.4877 |
| XIV | —(CH₂)₁₀CH₃ | 54 | 1.4857 |
| XV | —(CH₂)₁₁CH₃ | 42 | 1.4821 |
| XVI | —(CH₂)₁₃CH₃ | 41 | 1.4844 |
| XVII | —(CH₂)₂CH(CH₃)(CH₂)₃—CH(CH₃)(CH₂)₃CH(CH₃)₂ | 51 | 1.4621 |
| XVIII | —(CH₂)₈CH═CH(CH₂)₇CH₃ (Z—configuration) | 35 | 1.4834 |
| XIX | —(CH₂)₁₇CH₃ | 47 | (1) |
| XX | —CH(CH₃)(CH₂)₈CH₃ | 52 | 1.4695 |
| XXI | —(CH₂)₉CH═CH₂ | 40 | 1.4943 |

(1) mp. 34–36° C.

Example 12

Preparation of 1,2-dicarboxy-4-(4,8-dimethyl-3,7-nonadienyl)-cyclohex-4-ene (XXII)

A mixture of the Diels-Alder adduct of Example 6 (0.45 g) and a solution of sodium hydroxide (0.08 g, 2 eq) in water (45 ml) is stirred overnight to give the title compound (XXII) in the form of a solution of its disodium salt in water.

Example 13

Preparation of Diels-Alder adduct between (E)-β-farnesene and N-methoxycarbonylmaleimide (XXIII)

The (E)-β-farnesene-containing product of Example 1 (0.4 g) and N-methoxycarbonylmaleimide (0.2 g) are heated at 90° C. for 2 hours. The mixture is then chromatographed on Florisil (10 g) in hexane, eluting with increasing concentrations of ether in hexane, and the appropriate fractions of eluate evaporated to yield N-methoxycarbonyl-5-(4,8-dimethyl-3,7-nonadienyl)-Δ⁴-tetrahydrophthalimide as a pale yellow oil (0.22 g, 47%). NOTE: As an alternative to using this compound in a modification of type 8 described hereinbefore, or to using a modification of type 7 described hereinbefore, compounds containing a group —D—$CO_2R^1$ as described in modification 7), for example N-carboxymethyl-5-(4,8-dimethyl-3,7-nonadienyl-$\Delta^4$-tetrahydrophthalimide, may be prepared directly through a Diels-Alder reaction with a maleimide N— substituted by a group —D—$CO_2R^1$, for example with N-carboxymethyl maleimide which is accessible by reactions described in the art, such as those discussed under modification 7 for a sequence —NH——→—N($CO_2R$-)——→—N(D—$CO_2R^1$)—.

Example 14

Activity of (E)-β-farnesene on the settling of aphids (A) Air (20 ml) from a glass syringe containing a freshly broken ampoule of the (E)-β-farnesene-containing product of Example 1 (10 mg) was blown during a period of 10 seconds at colonies of various types of feeding aphids (ca 20) situated 1 cm from the tip of the syringe needle. The number of aphids that moved within 60 seconds was determined for 7 replicates, the results being given in Table 2 below as the percentage of the total number of aphids which moved within this period.

TABLE 2

| Aphid | Response (% ± standard error) |
|---|---|
| *Myzus persicae* (Sulz.) | 99 ± 0.6 |
| *Aphis fabae* Scop. | 71 ± 5.8 |
| *Phorodon humuli* (Schrank) | 78 ± 10.2 |
| *Sitobion avenae* (Fab.) (green) | 31 ± 11.7 |
| *Rhopalosiphum padi* (L.) | 47 ± 4.8 |
| *Nasonovia ribis-nigri* (Mosley) | 88 ± 5.9 |
| *Metopolophium dirhodum* (Walk.) | 61 ± 8.3 |

(B) Nitrogen (3 liters) was passed through a vessel containing a freshly broken ampoule of the (E)-β-farnesene-containing product of Example 1 (1 g) absorbed onto filter paper and the nitrogen was then blown at 230 mm/sec at 16 large plants of *Brassica pekinensis* infested with the aphid *Myzus persicae*. Over 90% of the aphids began to move about the plants after application of the (E)-β-farnesene.

Example 15

Activity of (E)-β-farnesene derivatives on the settling of aphids

The (E)-β-farnesene derivatives I to X and XIII were emulsified with water at 1% and 0.5% w/v concentration using 0.1% w/v of Ethylan BV as emulsifying agent and the emulsion was painted onto one half of a *Brassica pekinensis* leaf. The other half of the leaf was treated with emulsifier and water only. Aphids (*Myzus persicae*, ca 20) were placed on the leaf and their escape prevented by enclosing the leaf between two petri dishes. After 24 hours, the numbers of aphids settled on the two leaf halves were counted for 10 replicates. The results are given in Table 3 and show the numbers of aphids on the treated and control halves of the leaf for each derivative together with the statistical significance of difference, P.

TABLE 3

| Compound | Number of aphids settled control/treated | | Statistical significance of difference, P | |
|---|---|---|---|---|
| | 1% conc. | 0.5% conc | 1% conc | 0.5% conc |
| I | 11.4/3.6 | 9.8/8.6 | <0.001 | ns |
| II | 15.5/2.5 | 9.7/8.3 | <0.001 | ns |
| III | 15.9/2.8 | 10.7/6.5 | <0.001 | <0.05 |

TABLE 3-continued

| Compound | Number of aphids settled control/treated | | Statistical significance of difference, P | |
|---|---|---|---|---|
| | 1% conc. | 0.5% conc | 1% conc | 0.5% conc |
| IV | 9.4/2.3 | 12.2/4.6 | <0.01 | <0.01 |
| V | 13.4/1.6 | 13.6/3.3 | <0.001 | <0.001 |
| VI | 9.6/5.6 | 10.4/5.1 | <0.01 | <0.01 |
| VII | 14.4/1.9 | 13.2/4.2 | <0.001 | <0.01 |
| VIII | 11.3/1.8 | 12.7/6.0 | <0.01 | <0.01 |
| IX | 14.1/3.0 | 13.4/3.8 | <0.001 | <0.001 |
| X | 14.5/3.9 | 8.3/9.0 | <0.001 | ns |
| XIII | 16.1/2.6 | 12.2/5.4 | <0.001 | <0.01 |

The symbol ns indicates that, at that concentration, the results with the compound were not statistically different from those with the control. It will be seen therefore that all of the compounds show significant activity at 1% and most also show such activity at 0.5%.

The same procedure was carried out with the (E)-β-farnesene derivatives IX to XII and XIV to XIX at 0.5%, 0.1% and 0.05% w/v concentration. The probability values are shown in Table 4. In general, when differences were not statistically significant, experiments with that compound were not conducted at lower concentrations.

TABLE 4

| Compound | Statistical significance of difference. P | | |
|---|---|---|---|
| | 0.5% conc | 0.1% conc | 0.05% conc |
| X | ns | | |
| XI | <0.01 | ns | |
| XII | <0.01 | <0.05 | |
| IX | <0.001 | <0.001 | ns |
| XIV | <0.001 | <0.001 | <0.05 |
| XV | ns | | |
| XVI | <0.01 | | |
| XVII | ns | | |
| XVIII | <0.01 | ns | |
| XIX[1] | <0.05 | ns | |

[1] This compound was observed to give an aggregatory rather than a dispersant effect.

The symbol ns has the same meaning as in Table 3. It will be seen that the highest level of activity is to be found in the compounds containing an OR group of nine, ten or eleven carbon atoms, the level of activity being observed to increase with increasing carbon number for these three compounds. Reference to Table 3 shows that in the case of the $C_{10}$ compounds, the compound in which the six membered ring contains two double bonds (IX) is more active than that in which only one double bond is present (XIII).

Example 16

Activity of (E)-β-farnesene derivatives on the transfer of viruses by aphids

On pages 49 to 54 of volume 100 of the Annals of Applied Biology (1982) Gibson, Rice and Sawicki describe insecticide susceptible (S) and insecticide resistant ($R_1$ and $R_2$) clones of *M. persicae* as well as clones of the non-persistent potato virus Y (PVY) and the semi-persistent beet yellow virus (BYV). Gibson et al also describe a laboratory test for assessing the effects of compounds on virus uptake by the apterae of *M. persicae* and this procedure was applied to compounds I, II, III, IV, V, VI, VIII, IX, X and XIII as described hereinbefore in the Examples. Aphids were confined on half-leaves treated either with an emulsion (generally at 1% w/v) of the compound prepared using 0.1% w/v of Ethylan BV or with water containing the emulsifier only. Confinement on the leaves was for a period of 4 hours when testing for BYV acquisition and for 2.5 minutes when testing for PVY acquisition. To detect for virus acquisition the aphids were transferred to indicator seedlings and the number of plants infected by test and control aphids were compared.

The results are presented in Tables 5 and 6 where they are given as the difference from the control in percentage terms (a value of −25% indicating a reduction to three-quarters of the control figure and −75% indicating a reduction to one-quarter of the control figure). It will be seen that in the case of Table 5, relating to tests on the BVY virus, results for settling and nymph production are quoted as well as for virus infected plants.

It will be seen that some level of control of the transfer of virus was generally effected by the compounds and in Table 6 the control results were calculated to be statistically significant except in the one case utilising a 0.01% w/v concentration where a result was obtained for P which was not statistically significant (ns).

TABLE 5

Acquisition of BVY by the R1 resistant strain of *Myzus persicae*

| Compound[1] | Percentage difference from control | | |
|---|---|---|---|
| | Settling | Nymph production | Virus infected plants |
| II | −68 | −89 | −75 |
| I | −23 | −81 | −58 |
| VIII | −10 | −33 | −22 |
| V | −38 | −73 | −32 |
| X | −15 | −45 | −10 |
| III | −31 | −62 | −71 |
| I | −22 | −82 | −6 |
| VIII | −29 | −76 | −23 |
| V | −2 | −36 | +12 |
| X | −53 | −68 | −52 |
| VI | −11 | −51 | −2 |
| XIII | −41 | −64 | −26 |
| IX | −47 | −96 | −60 |
| III | −2 | −23 | −4 |
| IV | leaves destroyed | | |

[1]On tests of the first group the compound was applied to the leaves as a 1% w/v solution just before the test whilst in tests of the second group the compound was similarly applied but 24 hours before the test.

TABLE 6

Acquisition of PVY by the S susceptible strain and R1 and R2 resistant strains of *Myzus persicae*

| Compound[1] | Virus infected plants - percentage difference from control | | | Statistical significance of difference for combined results |
|---|---|---|---|---|
| | S | R1 | R2 | P |
| V | −57 | −77 | −96 | <0.001 |
| X | −20 | −65 | −42 | <0.001 |
| IX | −100 | −97 | −96 | <0.001 |
| IV | −56 | −75 | −68 | <0.001 |
| IX | −95 | −92 | −78 | <0.001 |
| IX | −95 | −93 | −92 | <0.001 |
| IX | −39 | −42 | −19 | <0.05 |
| IX | +12 | +12 | +12 | ns |

[1]In tests of the first group the compound was applied to the leaves as a 1% w/v solution just before the test, except for compound IX which was similarly applied seven days before the test. In the tests of the second group, which were run concurrently, compound IX was applied to the leaves just before the test at a concentration of 1% w/v, 0.1% w/v or 0.01% w/v (the results being given in descending order for descending concentration).

Example 17

Systemic activity of (E)-β-farnesene derivatives on the settling of aphids

Compounds V and XXII were tested, at 0.5% w/v concentration in the case of V and at 0.05% and 0.01% w/v in the case of XXIV, for systemic aphid settling activity by the following procedure. Leaves of *Brassica pekinensis* were severed from the plant under water to prevent air from entering the stem and the leaves were then split down the middle from the tip to halfway along their length. The leaves were then arranged in overlapping pairs through the positioning of the tip of one leaf halfway along the second with half of the upper part of the first leaf being arranged above the upper part of the second leaf and the other half of the upper part of the first leaf being arranged below the upper part of the second leaf through superimposing the splits present in each leaf. Once so positioned, the coincident splits in the two leaves were sealed lengthwise with Bluetack.

The pairs of leaves were then arranged with the stem of one leaf in the test solution and the stem of the other leaf in water and were allowed to remain like this for several hours (preliminary studies with red ink confirming that this procedure allows an even distribution throughout the leaf to occur). Once uptake had occurred, a petri dish containing 20 *Myzus persicae* apterae was placed above the upper halves of the two leaves, the dish thus covering an equal area of control and treated leaf. The number of aphids on each leaf were counted after 24 hours.

It was found that compound V used in this way exerted a phytotoxic effect at 0.5% w/v whilst compound XXII exerted a phytotoxic effect at this concentration and at 0.1% w/v. In order to be able to study the effect of compound XXII at 0.1% w/v concentration without the complication of phytotoxicity, the above procedure was used but with the leaves being retained on the plants and the plant roots being immersed in the test solution or water.

The results obtained are shown in Table 7, averaged over 10 replicates, where it will be seen that statistically significant evidence of systemic effect was obtained for compound XXII at 0.05% w/v and at 0.1% w/v (ns indicates a non-statistically significant result).

TABLE 7

| Compound | Concentration % w/v | Number of aphids settled control/treated | Statistical significance of difference P |
|---|---|---|---|
| V | 0.5 | 10.5/7.9 | ns |
| XXII | 0.05 | 11.5/4.5 | <0.05 |
| XXII | 0.01 | 8.7/8.3 | ns |
| XXII | 0.1[1] | 10.8/3.8 | <0.05 |

[1]Roots in test solution or water for control.

We claim:

1. A compound of the formula

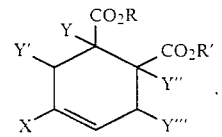

-continued

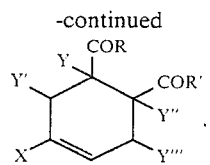

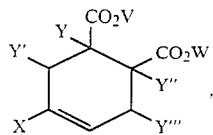

or

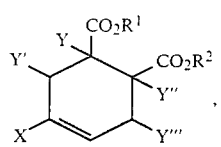

wherein X is 4,8-dimethyl-3,7-nonadienyl, Y, Y', Y" and Y''' are each hydrogen or any two of these which are adjacent form the second double bond of a carbon-carbon double bond joining the positions to which they are attached and the other two are hydrogen; R and R' are the same or different and each is unbranched or branched alkyl or alkenyl of up to 18 carbon atoms; V is $-(CH_2CH_2O)_{n'}H$ wherein n' is 1 to 10; W is the same or different $-(CH_2CH_2O)_{n'}H$ wherein n' is as above defined, or is unbranched or branched alkyl or alkenyl of up to 18 carbon atoms; and $R^1$ and $R^2$ are each hydrogen or one is hydrogen and the other is unbranched or branched alkyl or alkenyl of up to 18 carbon atoms.

2. A compound according to claim 1 wherein R and R' are unbranched alkyl of 8 to 14 carbon atoms.

3. A compound according to claim 1 wherein R and R' are unbranched alkyl of 8 to 12 carbon atoms.

4. A compound according to claim 1 wherein R and R' are unbranched alkyl of 9 to 11 carbon atoms.

5. A compound according to claim 1 of the formula

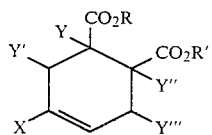

wherein X is 4,8-dimethyl-3,7-nonadienyl, Y, Y', Y" and Y''' are each hydrogen or any two to these which are adjacent form the second bond of a carbon-carbon double bond joining the positions to which they are attached and the other two are hydrogen, and R and R' are each unbranched or branched alkyl or alkenyl of up to 18 carbon atoms.

6. A compound according to claim 1 wherein $R^1$ and $R^2$ are each hydrogen and Y, Y', Y" and Y''' are each hydrogen or Y' and Y''' are hydrogen and Y and Y" together form the second bond of a carbon-carbon double bond.

7. A compound according to claim 5 of the formula

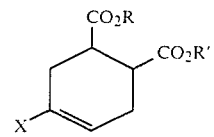

wherein X is 4,8-dimethyl-3,7-nonadienyl and R and R' are each unbranched or branched alkyl or alkenyl of up to 18 carbon atoms.

8. A compound according to claim 1 of the formula

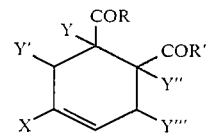

wherein X is 4,8-dimethyl-3,7-nonadienyl, Y, Y', Y" and Y''' are each hydrogen or any two of these which are adjacent form the second bond of a carbon-carbon double bond joining the positions to which they are attached and the other two are hydrogen, and R and R' are each unbranched or branched alkyl or alkenyl of up to 18 carbon atoms.

9. A compound according to claim 8 wherein Y, Y', Y" and Y''' are each hydrogen or Y' and Y''' are hydrogen and Y and Y" together form the second bond of a carbon-carbon double bond.

10. A compound according to claim 1, in which R and R' are each alkyl or alkenyl of eight to sixteen carbon atoms.

11. A compound according to claim 1, in which R and R' are each alkyl or alkenyl of nine, ten or eleven carbon atoms.

12. A compound according to claim 1, in which R and R' are each alkyl of up to 18 carbon atoms.

13. A compound according to claim 1, in which R and R' are each alkenyl of up to 18 carbon atoms.

14. A compound according to claim 1, in which R and R' are each either unbranched or branched solely at the carbon atom attached to the group $-CO_2-$ or $-CO-$.

15. A compound according to claim 1, in which R and R' are identical.

16. A compound according to claim 1 of the formula

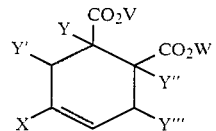

wherein X is 4,8-dimethyl-3,7-nonadienyl, Y, Y', Y" and Y''' are each hydrogen or any two of these which are adjacent form the second bond of a carbon-carbon double bond joining the positions to which they are attached and the other two are hydrogen, V is $-(CH_2CH_2O)_{n'}H$ in which n' is 1 to 10 and W is the same or different $-(CH_2CH_2O)_{n'}H$ wherein n' is as above defined, or unbranched or branched alkyl or alkenyl of up to 18 carbon atoms.

17. A compound according to claim 16 wherein Y, Y', Y" an Y''' are each hydrogen or Y' and Y''' are hydrogen and Y and Y″ together form the second bond of a carbon-carbon double bond.

18. A compound according to claim 16 wherein n′ is 1 to 6.

19. A compound according to claim 18 wherein V and W are the same —CH$_2$CH$_2$O)$_{n'}$H and n′ is 2, 3, or 4.

20. A compound according to claim 1 which contains a 4,8-dimethyl-3,7-nonadienyl group having the (E) configuration about the double bond at the 3,4 position.

21. A compound according to claim 1 wherein Y′ and Y‴ are each hydrogen, Y and Y″ form the second bond of a carbon-carbon double bond joining the position to which they are attached and R and R′ are each (CH$_2$)$_{10}$CH$_3$.

22. The compound according to claim 1 which is 1,2-bis-(nonyloxycarbonyl)-4[(E)-4,8-dimethyl-3,7-nonadienyl]cyclohexa-1,4-diene, 1,2-bis-(decyloxycarbonyl)-4-[(E)-4,8-dimethyl-3,7-nonadienyl]-cyclohexa-],4-diene, or 1,2-bis-(undecyloxycarbonyl)-4-[(E)-4,8-dimethyl-3,7-nonadienyl]cyclohexa-1,4-diene.

23. A pest control composition which comprises an effective amount of a compound of the formula

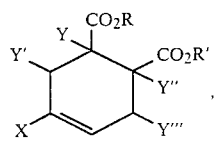

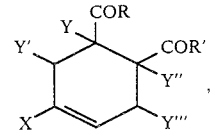

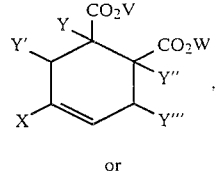

or

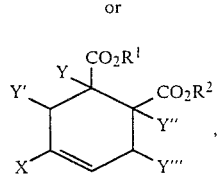

wherein X is 4,8-dimethyl-3,7-nonadienyl, Y, Y′, Y″ and Y‴ are each hydrogen or any two of these which are adjacent form the second double bond of a carbon-carbon double bond joining the positions to which they are attached and the other two are hydrogen; R and R′ are the same or different and each is unbranched or branched alkyl or alkenyl of up to 18 carbon atoms; V is —(CH$_2$CH$_2$O)$_{n'}$H wherein n′ is 1 to 10; W is the same or different —(CH$_2$CH$_2$O)$_{n'}$H wherein n′ is as above defined, or is unbranched or branched alkyl or alkenyl of up to 18 carbon atoms; and R$^1$ and R$^2$ are each hydrogen or one is hydrogen and the other is unbranched or branched alkyl or alkenyl of up to 18 carbon atoms, in combination with a suitable diluent or carrier.

24. A composition according to claim 23 wherein the compound is of the formula

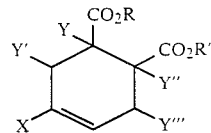

wherein X is 4,8-dimethyl-3,7-nonadienyl, Y, Y′, Y″ and Y‴ are each hydrogen or any two of these which are adjacent form the second bond of a carbon-carbon double bond joining the positions to which they are attached and the other two are hydrogen, and R and R′ are each unbranched or branched alkyl or alkenyl of up to 18 carbon atoms.

25. A composition according to claim 23 wherein R$^1$ and R$^2$ are each hydrogen and Y, Y′, Y″ and Y‴ are each hydrogen or Y′ and Y‴ are hydrogen and Y and Y″ together form the second bond of a carbon-carbon double bond.

26. A composition according to claim 24 wherein the compound is of the formula

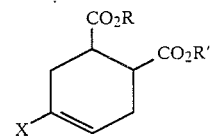

wherein X is 4,8-dimethyl-3,7-nonadienyl and R and R′ are each unbranched or branched alkyl or alkenyl of up to 18 carbon atoms.

27. A composition according to claim 23 which contains a 4,8-dimethyl-3,7-nonadienyl group having the (E) configuration about the double bond at the 3,4 position.

28. A composition according to claim 23 in which R and R′ are identical.

29. A composition according to claim 24 wherein Y′ and Y‴ are each hydrogen, Y and Y″ form the second bond of a carbon-carbon double bond joining the position to which they are attached and R and R′ are each (CH$_2$)$_{10}$CH$_3$.

30. A composition according to claim 23, in which R and R′ are each alkyl or alkenyl of eight to sixteen carbon atoms.

31. A composition according to claim 23, in which R and R′ are each alkyl or alkenyl of nine, ten or eleven carbon atoms.

32. A composition according to claim 23, in which R and R′ are each unbranched or branched solely at the carbon atom attached to the group —CO$_2$— or —CO—.

33. A composition according to claim 23 which additionally contains an effective amount of a pesticide.

34. A composition according to claim 23 wherein the compound is 1,2-bis-(nonyloxycarbonyl)-4-[(E)-4,8-dimethyl-3,7-nonadienyl]-cyclohexa-1,4-diene, 1,2-bis-(decyloxycarbonyl)-4-[(E)-4,8-dimethyl-3,7-nonadienyl]-cyclohexa-1,4-diene, or 1,2-bis-(undecyloxycarbonyl)-4-[(E)-4,8-dimethyl-3,7-nonadienyl]cyclohexa-1,4-diene.

35. A method for the control of crop damage by aphids which comprises applying to a crop in need of protection from such damage an effective amount of a compound of the formula

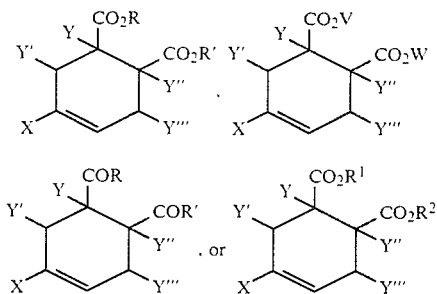

wherein X is 4,8-dimethyl-3,7-nonadienyl, Y, Y', Y" and Y'" are each hydrogen or any two of these which are adjacent form the second double bond of a carbon-carbon double bond joining the positions to which they are attached and the other two are hydrogen; R and R' are the same or different and each is unbranched or branched alkyl or alkenyl of up to 18 carbon atoms; V is —$(CH_2CH_2O)_{n'}H$ wherein n' is 1 to 10; W is the same or different —$(CH_2CH_2O)_{n'}H$ wheren n' is as above defined, or is unbranched or branched alkyl or alkenyl of up to 18 carbon atoms; and $R^1$ and $R^2$ are each hydrogen or one is hydrogen and the other is unbranched or branched alkyl or alkenyl of up to 18 carbon atoms.

36. A method according to claim 35 wherein the compound is of the formula

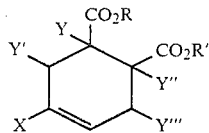

wherein X is 4,8-dimethyl-3,7-nonadienyl, Y, Y', Y" and Y'" are each hydrogen or any two of these which are adjacent from the second bond of a carbon-carbon double bond joining the positions to which they are attached and the other two are hydrogen, and R and R' are each unbranched or branched alkyl or alkenyl of up to 18 carbon atoms.

37. A method according to claim 35 wherein $R^1$ and $R^2$ are each hydrogen and Y, Y', Y" and Y'" are each hydrogen or Y' and Y'" are hydrogen and Y and Y" together form the second bond of a carbon-carbon double bond.

38. A method according to claim 36 the compound is of the formula

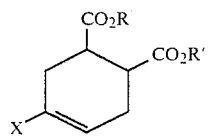

wherein X is 4,8-dimethyl-3,7-nonadienyl and R and R' are each unbranched or branched alkyl or alkenyl of up to 18 carbon atoms.

39. A method according to claim 35 wherein the compound contains a 4,8-dimethyl-3,7-nonadienyl group having the (E) configuration about the double bond at the 3,4 position.

40. A method according to claim 35 in which R and R' are identical.

41. A method according to claim 35 wherein Y' and Y'" are each hydrogen, Y and Y" form the second bond of a carbon-carbon double bond joining the position to which they are attached and R and R' are each $(CH_2)_{10}CH_3$.

42. A method according to claim 35, in which R and R' are each alkyl or alkenyl of eight to sixteen carbon atoms.

43. A method according to claim 35, in which R and R' are each alkyl or alkenyl of nine, ten or eleven carbon atoms.

44. A method according to claim 35, in which R and R' are each unbranched or branched solely at the carbon atom attached to the group —$CO_2$— or —CO—.

45. A method according to claim 35 wherein the compound is 1,2-bis-(nonyloxycarbonyl)-4-[(E)-4,8-dimethyl-3,7-nonadienyl]-cyclohexa-1,4-diene, 1,2-bis-(decyloxycarbonyl)-4-[(E)-4,8-dimethyl-3,7-nonadienyl]-cyclohexa-1,4-diene, or 1,2-bis-(undecyloxycarbonyl)-4-[(E)-4,8-dimethyl-3,7-nonadienyl]-cyclohexa-1,4-diene.

46. A method of aphid control which comprises applying to a crop in need of such control an effective amount of a compound of the formula

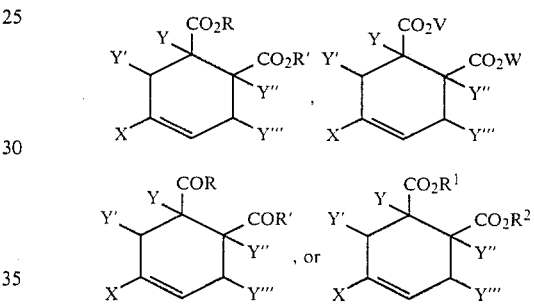

wherein X is 4,8-dimethyl-3,7-nonadienyl, Y, Y', Y" and Y'" are each hydrogen or any two of these which are adjacent form the second double bond of a carbon-carbon double bond joining the positions to which they are attached and the other two are hydrogen, R and R' are the same or different and each is unbranched or branched alkyl or alkenyl of up to 18 carbon atoms; V is —$(CH_2CH_2O)_{n'}H$ wherein n' is 1 to 10; W is the same or different —$(CH_2CH_2O)_{n'}H$ wherein N' is as above defined, or is unbranched or branched alkyl or alkenyl of up to 18 carbon atoms; and $R^1$ and $R^2$ are each hydrogen or one is hydrogen and the other is alkyl or alkenyl of up to 18 carbon atoms, in combination with an effective amount of a pesticide.

47. A method according to claim 46 wherein the compound is of the formula

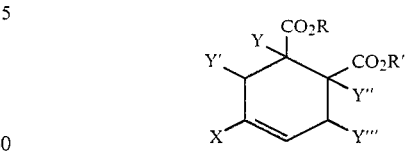

wherein X is 4,8-dimethyl-3,7-nonadienyl, Y, Y', Y" and Y'" are each hydrogen or any two of these which are adjacent form the second bond of a carbon-carbon double bond joining the positions to which they are attached and the other two are hydrogen, and R and R' are each unbranched or branched alkyl or alkenyl of up to 18 carbon atoms.

48. A method according to claim 46 wherein $R^1$ and $R^2$ are each hydrogen and Y, Y', Y" and Y'" are each hydrogen or Y' and Y'" are hydrogen and Y and Y" together form the second bond of a carbon-carbon double bond.

49. A method according to claim 46 wherein the compound contains a 4,8-dimethyl-3,7-nonadienyl group having the (E) configuration about the double bond at the 3,4 position.

50. A method according to claim 46 wherein the compound is 1,2-bis-(nonyloxycarbonyl)-4-[(E)-4,8-dimethyl-3,7-nonadienyl]-cyclohexa-1,4-diene, 1,2-bis-(decyloxycarbonyl)-4-[(E)-4,8-dimethyl-3,7-nonadienyl-cyclohexa-1,4-diene, or 1,2-bis-(undecyloxycarbonyl)-4-[(E)-dimethyl-3,7-nonadienyl]-cyclohexa-1,4-diene.

51. A compound according to claim 5 of the formula

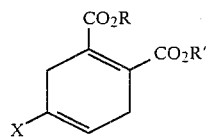

wherein X is 4,8-dimethyl-3,7-nonadienyl and R and R' are each unbranched or branched alkyl or alkenyl of up to 18 carbon atoms.

52. A composition according to claim 24 wherein the compound is of the formula

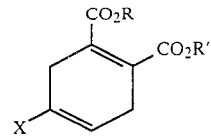

wherein X is 4,8-dimethyl-3,7-nonadienyl and R and R' are each unbranched or branched alkyl or alkenyl of up to 18 carbon atoms.

53. A method according to claim 36 wherein the compound is of the formula

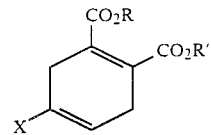

wherein X is 4,8-dimethyl-3,7-nonadienyl and R and R' are each unbranched or branched alkyl or alkenyl of up to 18 carbon atoms.

* * * * *